US00PP14858P2

(12) United States Plant Patent
Sakazaki

(10) Patent No.: US PP14,858 P2
(45) Date of Patent: Jun. 1, 2004

(54) PETUNIA PLANT NAMED 'MEDIOPIMO'

(50) Latin Name: *Petunia×hybrida*
Varietal Denomination: Mediopimo

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/638,684

(22) Filed: Aug. 11, 2003

(51) Int. Cl.[7] ..... A01H 5/00
(52) U.S. Cl. ..... Plt./356
(58) Field of Search ..... Plt./356

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Petunia plant named 'Mediopimo', characterized by its semi-upright to cascading plant habit; freely branching habit; numerous single flowers that are bright pink in color; and good garden performance.

1 Drawing Sheet

Botanical classification/cultivar designation: Petunia×hybrida cultivar Mediopimo.

BACKGROUND OF THE INVENTION

The present Invention relates to a new and distinct cultivar of Petunia plant, botanically known as Petunia×hybrida, and hereinafter referred to by the cultivar name Mediopimo.

The new Petunia is a product of a planned breeding program conducted by the Inventor in Hikone, Shiga, Japan. The objective of the breeding program is to create new disease-resistant and heat-tolerant Petunias with semi-upright plant habit and attractive flower colors.

The new Petunia originated from a cross-pollination made by the Inventor in December, 1998 of the Petunia cultivar Fantasy Pink Morn, not patented, as the female, or seed parent, with an unnamed selection of Petunia, not patented, as the male, or pollen parent. The new Petunia was selected as a single plant from the resulting progeny in September, 1999 in Gensingen, Germany, on the basis of its plant habit and attractive flower coloration.

Asexual reproduction of the new cultivar by terminal vegetative cuttings since September, 1999, taken in Gensingen, Germany has shown that the unique features of this new Petunia are stable and reproduced true to type in successive generations.

SUMMARY OF THE INVENTION

Plants of the cultivar Mediopimo have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Mediopimo'. These characteristics in combination distinguish 'Mediopimo' as a new and distinct cultivar:

1. Semi-upright to cascading plant habit.
2. Freely branching habit.
3. Numerous single flowers that are bright pink in color.
4. Good garden performance.

In side-by-side comparisons conducted in Hikone, Shiga, Japan, plants of the new Petunia differed from plants of the female parent, the cultivar Fantasy Pink Morn, in the following characteristics:

1. Plants of the new Petunia were more cascading than and not as upright as plants of the cultivar Fantasy Pink Morn.
2. Plants of the new Petunia were more vigorous than plants of the cultivar Fantasy Pink Morn.

In side-by-side comparisons conducted in Hikone, Shiga, Japan, plants of the new Petunia differed from plants of the male parent selection in the following characteristics:

1. Plants of the new Petunia were more vigorous than plants of the male parent selection.
2. Plants of the new Petunia had larger flowers than plants of the male parent selection.

Plants of the new Petunia can be compared to plants of the cultivar Surfinia Pink Mini, not patented. In side-by-side comparisons conducted in Gensingen, Germany, plants of the new Petunia differed from plants of the cultivar Surfinia Pink Mini in the following characteristics:

1. Plants of the new Petunia were not as vigorous and were more compact than plants of the cultivar Surfinia Pink Mini.
2. Plants of the new Petunia had smaller flowers than plants of the cultivar Surfinia Pink Mini.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Petunia.

The photograph at the top of the sheet comprises a side perspective view of three typical plants of 'Mediopimo' grown in a container.

The photograph at the bottom of the sheet is a close-up view of typical flowers and leaves of 'Mediopimo'.

DETAILED BOTANICAL DESCRIPTION

The aforementioned photographs and following observations and measurements describe plants grown in Bonsall, Calif., in an outdoor nursery during the spring and summer under full sun conditions with day temperatures ranging from about 18 to about 35° C. and night temperatures ranging from about 10 to about 18° C. After planting rooted cuttings, plants were grown for about eight weeks in 15-cm containers with three plants per container. Color references are made to The Royal Horticultural Society Colour Chart, 1995 Edition, except where general terms of ordinary dictionary significance are used.

Botanical classification: Petunia×hybrida cultivar Mediopimo.

Parentage:

*Female parent.*—Petunia×hybrida cultivar Fantasy Pink Morn, not patented.

*Male parent.*—Unnamed selection of Petunia×hybrida, not patented.

Propagation:

*Type cutting.*—Terminal vegetative cuttings.

*Time to initiate roots, summer and winter.*—About 15 days at 20 to 22° C.

*Time to develop roots, summer and winter.*—About 20 days at 18 to 20° C.

*Root description.*—Fine; white, close to 155D, in color.

*Rooting habit.*—Freely branching.

Plant description:

*Form.*—Annual flowering plant; indeterminate; initially upright, then semi-upright to outwardly spreading and cascading; uniformly mounded plant form. Freely branching habit with about four to five lateral branches and numerous secondary lateral branches per plant. Pinching will enhance development of lateral branches.

*Usage.*—Appropriate for hanging baskets, window boxes, patio containers and landscape applications.

*Plant height.*—About 11 cm.

*Plant diameter* (*area of spread*), *single plant.*—About 23 cm.

*Vigor.*—Vigorous; moderately rapid growth rate.

*Lateral branches.*—Length: About 22 cm. Diameter: About 2.5 mm. Internode length: About 1.5 to 3.5 cm. Texture: Pubescent. Color: 144D.

*Foliage description.*—Arrangement: Alternate before flowering; opposite after flowers develop; simple. Length: About 3.8 cm. Width: About 2.1 cm. Shape: Elliptic. Apex: Rounded to broadly acute. Base: Attenuate. Margin: Entire. Texture, upper and lower surfaces: Glabrous; glandular; slightly rough. Venation pattern: Pinnate, arcuate. Color: Developing leaves, upper surface: 146A. Developing leaves, lower surface: 146C. Fully expanded leaves, upper surface: 146A. Fully expanded leaves, lower surface: 147B. Venation, upper and lower surfaces: 144B. Petiole length: About 6 mm. Petiole diameter: About 3 mm. Petiole color: 144D.

Flower description:

*Flower type and habit.*—Single salverform flowers; flowers face mostly upward or outward; axillary. Freely flowering habit, about three to four open flowers and about 16 to 18 flower buds per lateral branch at one time.

*Natural flowering season.*—Long day responsive; long flowering period, spring until frost in the autumn; flowering continuous during this period. Plants start flowering about four to six weeks after planting rooted cuttings. Flowers persistent.

*Flower longevity on the plant.*—About five to seven days.

*Fragrance.*—Faint; sweet floral.

*Flower size.*—Diameter: About 5 cm. Tube length: About 2.5 cm. Throat diameter, distal end: About 1.3 cm. Tube diameter, proximal end: About 4 mm.

*Flower buds.*—Length: About 2 cm. Diameter: About 5.5 mm. Shape: Elongated oblong with ruffled apices. Color: 82C.

*Petals.*—Quantity/arrangement: About five petals fused in a single whorl, funnelform. Length from throat: About 2.4 cm. Width: About 2 cm. Shape: Roughly fan-shaped. Apex: Broadly acute. Margin: Entire. Texture, upper and lower surfaces: Smooth, velvety. Color: When opening, upper surface: 74C. When opening, lower surface: 75C to 75D. Fully opened, upper surface: 73A, towards the throat, 75C; color becoming closer to 80D with development. Fully opened, lower surface: 75D. Flower throat (inside): 155A. Flower tube (outside): 157A to 157B. Venation, upper petal surface: 73A. Venation, lower petal surface: 144C. Venation, throat: 145B. Venation, tube: 145B.

*Sepals.*—Arrangement/appearance: Single whorl of five sepals fused at base, star-shaped. Length: About 1.5 cm. Width: About 4.5 mm. Shape: Linear to obovate. Apex: Rounded. Margin: Entire. Texture, upper and lower surfaces: Pubescent. Color, upper surface: 146A. Color, lower surface: 146B.

*Peduncles.*—Length: About 3.8 cm. Width: About 1.2 mm. Angle: About 45° from the stem. Strength: Strong. Texture: Pubescent. Color: 144C.

*Reproductive organs.*—Stamens: Quantity per flower: About five. Anther shape: Ovoid. Anther length: About 1.5 mm. Anther color: 155A. Pollen amount: Scarce to moderate. Pollen color: 2D. Pistils: Quantity per flower: One. Pistil length: About 1.5 cm. Style length: About 1.3 cm. Style color: 144D. Stigma shape: Anvil-shaped. Stigma color: 144C. Ovary color: 144B.

*Seed/fruit.*—Seed and/or fruit production has not been observed.

Disease/pest resistance: Plants of the new Petunia have not been noted to be resistant to pathogens or pests common to Petunia.

Garden performance: Plants of the new Petunia have been observed to have good garden performance. Plants of the new Petunia have been noted to tolerate temperatures from 0 to 38° C. and have excellent tolerance to rain and wind.

It is claimed:

1. A new and distinct cultivar of Petunia plant named 'Mediopimo', as illustrated and described.

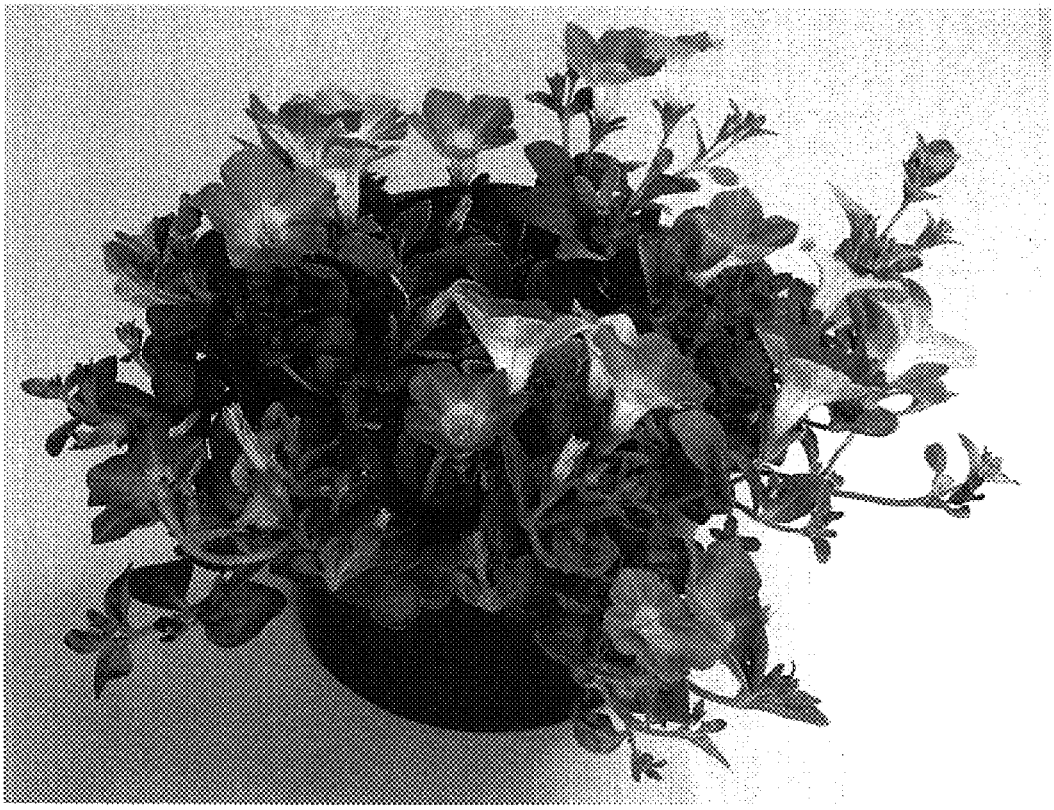
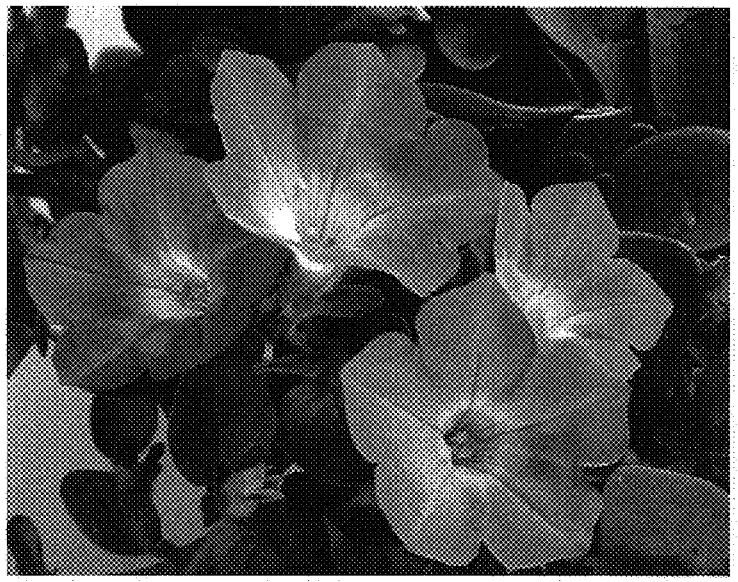

* * * * *